United States Patent [19]

Seemann

[11] 4,263,804
[45] Apr. 28, 1981

[54] APPARATUS FOR DIRECTLY MEASURING DENSITY ALTITUDE IN AN AIRCRAFT

[76] Inventor: Robert A. Seemann, 89 Earl Ave., Hamden, Conn. 06514

[21] Appl. No.: 73,622

[22] Filed: Sep. 10, 1979

[51] Int. Cl.³ .......................... G01N 9/00; G01C 5/00
[52] U.S. Cl. ...................................... 73/30; 73/178 H; 73/384
[58] Field of Search .................. 73/30, 32 R, 178 H, 73/178 R, 181, 179, 384

[56] References Cited

U.S. PATENT DOCUMENTS

| | | | |
|---|---|---|---|
| 1,648,693 | 11/1927 | McNairy | 73/30 |
| 2,123,038 | 7/1938 | Dallmann | 73/30 |
| 2,465,775 | 3/1949 | White | 73/30 |
| 3,590,636 | 7/1971 | Eddy | 73/178 H |

Primary Examiner—James J. Gill

[57] ABSTRACT

The invention resides in apparatus for directly measuring density altitude in an aircraft and includes a housing in communication with ambient conditions of air temperature, pressure and humidity outside the aircraft. A rotor having dynamically balanced blade elements is positioned rotatably within the housing. An electric motor is connected so as to drive the rotor within the housing against the resistance therein of the air under the ambient conditions of temperature, pressure and humidity. An operational characteristic of the motor, such as the current which it draws, is continuously sampled, amplified and changed in shape and applied as the input to a display device which is calibrated to display the input in terms of density altitude.

9 Claims, 3 Drawing Figures

APPARATUS FOR DIRECTLY MEASURING DENSITY ALTITUDE IN AN AIRCRAFT

BACKGROUND OF THE INVENTION

The present invention relates to the direct measurement of density altitude and more particularly to a method and apparatus for directly measuring density altitude.

As is known, the conventional altimeter is basically nothing more than an aneroid barometer having a display face which is graduated in feet of altitude instead of in inches of mercury. Inasmuch as the altimeter is essentially a barometer it provides an indication of altitude which corresponds to the existing atmospheric pressure (ambient conditions of pressure) surrounding the aircraft. Altimeters are customarily calibrated based upon the International Standard Atmosphere which is premised upon a sea-level pressure of 29.92 inches of mercury and a temperature of 59° F. Calculators are available which, by manipulation, take into account a temperature change of 2° C. per thousand feet of altitude change. In such manner temperature compensation for variation in altitude may be introduced. Further, it is conventional to provide for changes in barometric pressure between locations along the flight route by adjustment of the display face, i.e. the Kollsman window to the barometric pressure of the geographic location where the reading is to be made. The altimeter will then provide a reading on its face which is commonly referred to as indicated altitude. However, such reading does not accurately reflect the temperature conditions at the specific altitude and location where the reading is taken nor does it take into account conditions of relative humidity. Temperature and humidity are extremely important factors to be considered since changes in humidity alone can have a significant influence upon the performance of the aircraft. In order to obtain the density altitude it has been conventional heretofore to first obtain an irdication of pressure altitude and then resort to manual computation, charts or complex auxiliary equipment to secure the density altitude.

It has been ascertained, for example, that the hovering ceiling of a helicopter having a gross weight of 1600 pounds changes from 3000 feet under conditions of dry air to only 1300 feet when the atmosphere has changed to 80% relative humidity. This is attributable solely to the variation in the air density due to the increase in humidity. Thus, a helicopter maintaining sufficient lift at cruising speed could have insufficient power to hover to a landing under conditions of high density altitude, and would instead be compelled to make a running landing so as to utilize effective transitional lift. On the other hand, a fixed wing aircraft may be able to utilize ground effect during takeoff but may encounter difficulty in clearing obstacles normally surmounted because high density altitude conditions prevent the aircraft from establishing a safe angle of climb for its gross weight even with maximum power.

It will thus be seen that an indication of pressure altitude alone is not sufficient to provide the pilot with adequate information upon which to make decisions affecting takeoff, landing and cruising of the aircraft. Without an accurate indication of density altitude there is an ever present risk of accident. It is estimated that a significant number of accidents each year are directly attributable to either a lack of information concerning density altitude or an inability to secure such information quickly and easily. Even those charts and apparatuses available heretofore for the determination of density altitude frequently made no provision for changes in humidity and took into account only barometric pressure and temperature.

In view of the foregoing it is one object of this invention to provide apparatus for directly measuring and displaying density altitude taking into consideration the factors of pressure, temperature and humidity.

It is another object of the invention to provide apparatus of the character described which is simple in construction and rugged such that it can be installed in an aircraft and be capable of reliable performance while being subjected to the normally contemplated flight conditions of the aircraft.

It is yet another object of the invention to provide a method for directly measuring density altitude and for providing a direct readout thereof.

Other objects and advantages of the invention will become readily apparent to persons skilled in the art from the ensuing description.

SUMMARY OF THE INVENTION

In accordance with the invention there is provided apparatus for directly measuring and displaying density altitude which comprises a housing that is in communication with ambient conditions of temperature, pressure and humidity. A rotor having dynamically balanced blade elements integral therewith is mounted within the housing. An electric motor is drivably connected to the rotor for imparting rotational movement thereto. An amplifier/shaper monitors changes in at least one operational characteristic of the motor and amplifies and shapes the data being monitored to produce a continuous signal. Such signal is applied as the input to a display device which is calibrated to display density altitude representative of the input signals.

BRIEF DESCRIPTION OF THE DRAWINGS

In order that the invention may be more fully comprehended it will now be described, by way of example, with reference to the accompanying drawings in which.

DESCRIPTION OF THE PREFERRED EMBODIMENTS

Figure 1:
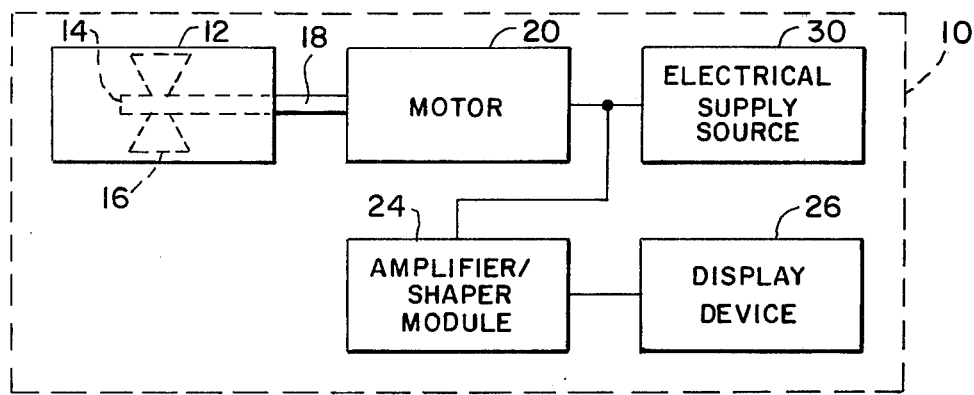
FIG. 1 is a schematic illustration of apparatus embodying the features of the invention in one of its preferred forms.

Before explaining the invention in detail it is to be understood that the invention is not limited in its application to the details of construction and arrangement of parts illustrated in the drawings since the invention is capable of other embodiments and of being practiced or carried out in various ways. It is also to be understood that the phraseology or terminology employed is for purposes of description only and not of limitation.

Referring to the drawings, in which like parts are similarly designated, there is shown a device 10 for directly measuring and displaying a direct reading of density altitude. The device includes a rotor housing or cage 12 which is in communication with the ambient atmosphere by any convenient expedient. Within the housing there is positioned a rotor 14 capable of rotation therein. The rotor is provided with a series of blade elements 16 which may be of any suitable design which insures that upon rotation of the rotor such blade elements encounter the resistance of the atmosphere within the housing and transmit such resistance to motor shaft 18 of motor 20 thereby affecting the rotational speed of the motor and/or the power consumption of the motor, e.g. the total power required to continuously drive the motor at a constant speed such as the current drawn by the motor, etc.

Connected to the motor so as to continuously monitor one of its operational characteristics such as motor speed, voltage or current and to convert same to a form suitable as input signals for a display device 26 is an amplifier/shaper module 24. The output signals of module 24 are thus matched to the input requirements of a display module 26 which is itself calibrated so as to display density altitude in terms of feet or any other desired units.

It will be recognized, of course, that the housing 12 may be constructed as a closed chamber with an orifice therein of sufficient size to assure maintenance within the chamber of pressure, temperature and humidity conditions which are the same as, or directly proportional to, or a function of the ambient atmosphere at the pressure altitude at which the aircraft is operating. It is thus within the contemplation of the invention to employ a simple cage-type housing freely communicating with the atmosphere. The blade elements 16 may desirably comprise paddles or vanes integral with the rotor body or, as stated earlier, such blade elements may take any suitable form which will insure that due to the dynamic resistance of the air within the housing such resistance will be transmitted to the motor. By measuring the effect of such resistance upon the motor through the monitoring of a selected operational characteristic thereof as described earlier it will be seen that the effect of temperature, pressure altitude and humidity are automatically taken into consideration in the determination of density altitude and translated into a visual indication of density altitude as displayed on device 26. The density thus displayed provides an extremely accurate and direct reading of the density altitude at which the aircraft's airfoils, e.g. propeller, rotor, wings must perform.

Figure 3:
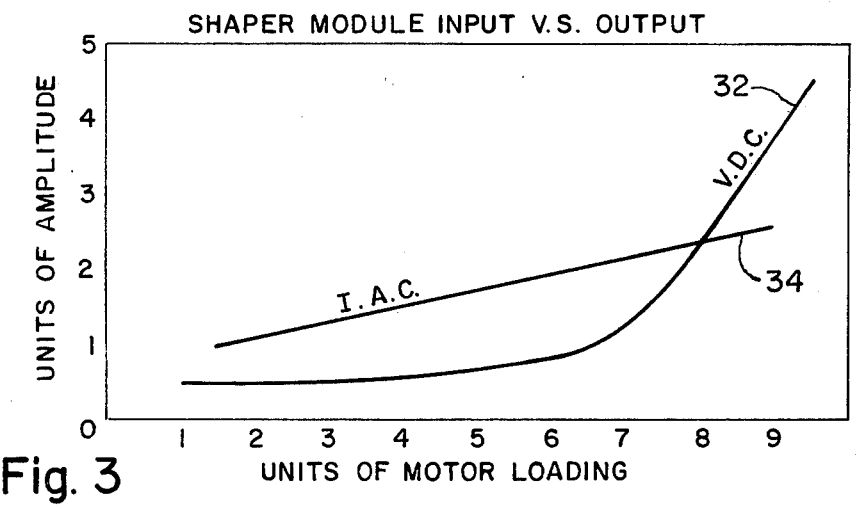
FIG. 3 is a graph showing the shaping of a voltage output for application to a display device.

A preferred embodiment of the invention is shown in FIG. 1 and will now be described. The blade elements 16 are driven by the motor 20 at a high velocity; however, the tips of the blade elements should not be driven at a velocity which is greater than Mach 1. The motor is of the synchronous type and thus operates at a substantially constant speed although, as will be appreciated, there may be momentary changes in speed as the loading of the motor shaft varies. The resistance to rotation of the blade or paddle elements is transmitted to the motor via the shaft 18. Given a constant AC voltage and a source of electrical supply 30 which will also provide a constant frequency the current drawn by the motor will vary with shaft loading so as to increase with increased load and decrease with decreased loading of the shaft. The changes in AC current drawn by the motor and its amplification and shaping by module 24 are depicted graphically in FIG. 3. As described earlier, the function of module 24 is to match the input requirements of display device 26 so that the display can provide a reading through the complete density altitude range to be exhibited for the sampled current changes of the motor. FIG. 3 thus shows the shaping of voltage output 32 to be applied as input to display 26 which requires a logarithmic DC input in order to display density altitude relative to a linear, low-change average AC current input 34 which varies with changes in motor loading during the continuous sampling of motor current.

It will, of course, be appreciated that to facilitate production of the apparatus of the invention, and depending upon the selection of a particular type of motor and display device, any suitable AC or DC amplifier and/or Delta voltage or current shaping module commercially available may be employed to process the sampled motor voltage or current for matching to the input of the display device. It will also be recognized that the display unit may provide digital or other readout information but should be calibrated to display the information in terms of density altitude.

Module 24 should be capable of carrying out up to three functions. First, it should be capable of amplifying the characteristic being sampled. For example, when the sampled AC voltage or DC voltage or current flow does not have sufficient magnitude to fall within the sensitivity range of the display unit amplification is required. Second, the amplitude of the signal for the selected characteristic across the motor load range must be shaped to provide the proper display-readout voltage level for each corresponding load. For example, the display device may require from approximately 1 volt to approximately 5 volts in order to afford readings for the complete altitude range under consideration; however, the voltage obtained from the sampled motor characteristic may vary only from a minimum of approximately 0.1 volt to a maximum of approximately 0.2 volts through the motor speed range of motor 20. Thus, when amplified by a factor of 10 the lowest voltage of 0.1 volt is converted to 1 volt and will be representative of the correct lowest corresponding altitude indication. The 0.2 volt upper value is converted to 2 volts; however, although it correctly represents the highest corresponding altitude it will not be properly displayed since the display unit requires 5 volts to correctly display such upper altitude. The shaping portion of the module must, therefore, be capable of amplifying the voltage but at different magnitudes for different input voltages. It must be capable of amplifying the 0.1 volt input by a factor of 10 and also increase the amplification factor upwardly through the range of increasing input voltages such that the input voltage representing the upper limit of the display range, i.e. 0.2 volts is amplified by a factor of 25. It will then provide the 5 volts necessary to properly display the upper altitude value. It will, therefore, become apparent that the rate of change or Delta V of the input voltage to the amplifier/shaper module will be represented by a different Delta V from the module 24 to display unit 26 and that a Delta V input may be represented by logarithmic Delta V output. Further, it will be appreciated that the Delta V input to module 24 will possess a particular change function which may or may not be directly proportional to the change in altitude but instead may be a known function of a characteristic such as blade element performance, motor characteristics' electrical curve or any other selected electrical or mechanical parameter of the system. The shaping portion of the module, therefore, is necessary to interpret the input Delta voltage function into a new function required by the display unit in order to provide the correct readout through the altimeter's altitude range. Finally, a third capability of the shaper- /amplifier should be to convert AC voltage to DC voltage or vice versa if so required depending upon the motor characteristic being sampled and the input requirements of the display device.

Although FIG. 1 illustrates one preferred form of the invention it will be understood that a variety of arrangements is possible. For example, the motor may be a constant speed motor with a feedback control loop. The feedback signal may be derived from an extra set of motor windings or from a mechanically coupled generator. The feedback signal produced thus serves as a control for the motor power supply, providing an increase in such electrical supply to the motor as the load upon the motor increases and decreasing the electrical supply with decreases in load. The amplifier/shaper module 24 may be connected either to the feedback loop or to the primary electrical supply circuit. It will be understood, of course, that the voltage at the point of feedback for regulation of the motor power supply is measured as an inverse factor to loading since it will decrease with a decrease in motor speed whereas voltage measured from the point of the regulated supply to the motor correlates directly with loading, such voltage increasing in order to maintain the motor under constant speed conditions with increased load.

Another alternative to the embodiment depicted in FIG. 1 comprises providing a constant electrical supply source and use of a motor which is constructed so as to have its speed vary with the loading imposed thereon. The speed of the motor may be sensed directly electrically such as by sampling the speed in terms of the voltage from an extra set of windings or from a mechanically coupled generator. A decrease in motor speed will result from an increase in the density of the air within the housing (corresponding to ambient conditions) indicating a lower density altitude. On the other hand, as the density altitude increases there will be a corresponding increase in motor speed since the actual density of the air within the housing in such event will decrease. The motor speed will never attain its maximum for the motor selected since this would only occur when the blade elements are rotating under vacuum conditions such as if the aircraft is in outer space. The sampled voltage is shown, after amplification and the required shaping, on the display device which is calibrated in terms of density altitude. Higher voltages obtained from sampling are correlated with higher density altitude.

Figure 2:
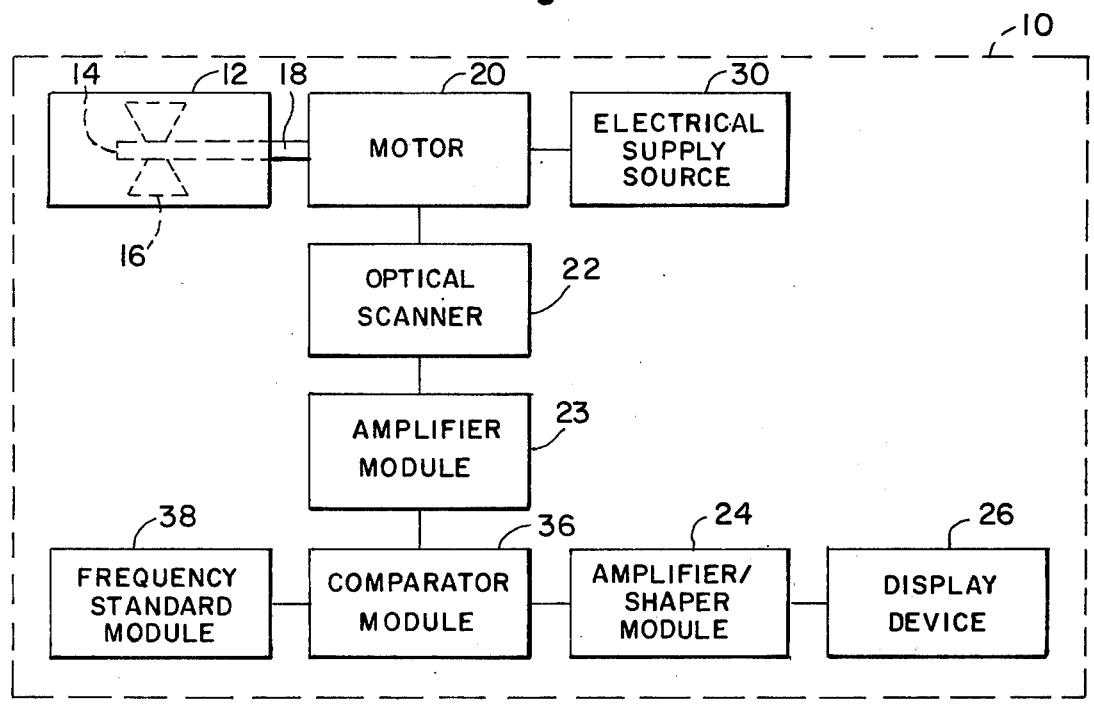
FIG. 2 is a view similar to that of FIG. 1 showing the invention in an alternate embodiment.

Yet another embodiment of the invention is shown in FIG. 2 and comprises the provision of a constant source of electrical supply 30 and a motor 20 whose speed is variable with motor loading. The motor speed may be sensed by means of a magnetic or optical scanner 22 which scans predetermined points on the motor shaft or on some other suitable portion of the rotor or an extension thereof. A comparator module 36 may be connected with the sensing circuit by means of an amplifier module 23 and is used to compare the amplified sensor output with that which is obtained from a frequency standard module 38 to thereby provide a varying voltage related to variations in motor speed. The type of comparator module 36 selected may provide either increased or decreased voltage in response to relative changes in frequency between the amplifier 23 and the frequency standard module 38. The output of comparator module 36 is amplified and shaped in module 24 as is necessary to match the voltage range input of the density altitude display unit as described earlier.

Still another embodiment involves the use of a vacuum driven constant speed motor to drive the rotor. The motor load-related voltage is derived from a constant voltage supplied resistance bridge which may be mechanically coupled to a vacuum control valve employed to adjust the vacuum as required in order to maintain a constant motor speed. On the other hand, the vacuum driven motor may be of the variable speed type and supplied by a fixed vacuum. The sampled voltage may be derived from a coupled generator as described above in connection with the determination of the speed of the variable speed motor through direct electrical sensing or by the sensing technique described above in connection with the use of a scanning device.

The method of the invention comprises monitoring a component of the power consumption of the driving motor such as the current which it draws under load or its voltage, either directly or indirectly, amplifying and shaping the signals which are representative of the component being monitored, and matching the thus amplified and shaped signals to an appropriate display device that is calibrated to provide a visual indication of density altitude in terms of feet or any other desired units.

From the foregoing it will be seen that the invention provides a device and method for the direct measurement and display of density altitude which obviates the need to resort to charts and auxiliary devices as is required presently after first obtaining the pressure altitude. The invention thus eliminates the customary delay necessitated in the manual computation of density altitude from pressure altitude and automaticaly takes into consideration the factor of humidity in addition to pressure altitude and temperature which latter factors only are conventionally considered in the calculation of density altitude.

Although the invention has been described in specific terms it will be understood that various changes may be made in size, shape, materials and in the arrangement of the parts without departing from the spirit and scope of the invention as claimed.

Having thus set forth the nature of the invention, what is claimed herein is:

1. Apparatus for directly measuring and displaying density altitude in an aircraft comprising:
    a housing in communication with ambient conditions of air temperature, pressure and humidity outside the aircraft;
    a rotor having dynamically balanced blade elements thereon mounted rotatably within said housing;
    electric motor means drivably connected to said rotor for imparting rotational movement thereto;
    means for monitoring at least one selected operational characteristic of said motor and for producing signals representative of such selected operational characteristic;
    and display means responsive to said signals for directly displaying the density altitude outside the aircraft.

2. Apparatus according to claim 1, wherein said electric motor means comprises a constant speed motor and said monitoring means includes means for sampling a power consumption factor of said motor and means for amplifying and shaping said power consumption factor to match the range of said display means.

3. Apparatus according to claim 2, wherein said power consumption factor comprises the current drawn by said motor under conditions of load.

4. Apparatus according to claim 2, wherein said power consumption factor comprises the motor voltage under conditions of load.

5. Apparatus according to claim 1, 2, 3 or 4, including a feedback loop for said motor.

6. Apparatus according to claim 1, including a source of constant electrical power, said motor being a variable speed motor, and said means for monitoring including means for sampling a motor voltage which reflects corresponding motor speed and for amplifying and shaping the sampled voltage to match the range of said display means.

7. Apparatus for directly measuring and displaying density altitude comprising:
- a housing in communication with ambient conditions of temperature, pressure and humidity;
- a rotor having dynamically balanced blade elements thereon mounted rotably within said housing;
- electric motor means drivably connected to said rotor for imparting rotational movement thereto;
- means for continuously monitoring changes in at least one selected operational characteristic of said motor and for producing signals representative of such changes;
- and means for receiving the signals produced by said monitoring and signal producing means as the input thereof and for displaying said signals through a predetermined range in terms of density altitude;
- and including a constant source of electrical supply connected to said motor, said motor being a motor the speed of which is variable with loading thereon, sensing means for sensing the speed of said motor and for producing signals representative thereof, a frequency standard, a comparator connected operatively with said frequency standard and with said sensing means for comparing the frequencies thereof and for producing output signals representative of the differences between said frequencies, and amplifying and shaping means adapted to receive the output signals of said comparator and to amplify and shape said output signals and apply the thus amplified and shaped signals to said display means.

8. Apparatus according to claim 7, including an amplifier interposed between said sensing means and said comparator for amplifying the sensed signals.

9. Apparatus for directly measuring and displaying density altitude in an aircraft comprising:
- a housing in communication with ambient conditions of air temperature, pressure and humidity outside the aircraft;
- a rotor having dynamically balanced blade elements thereon mounted rotatably within said housing;
- vacuum motor means drivably connected to said rotor and being effective for imparting rotational movement thereto, said vacuum motor means including a vacuum motor the speed of which is variable with loading thereon;
- means for monitoring said speed and for producing signals representative thereof;
- and means responsive to said signals for directly displaying said density altitude.

* * * * *